US005242389A

United States Patent [19]

[11] Patent Number: 5,242,389

[45] Date of Patent: Sep. 7, 1993

Schrader et al.

[54] ENTERAL FEEDING TUBE ENTERAL FEEDING TUBE WITH SEPARATE STYLET LUMEN

[75] Inventors: Eugene F. Schrader, St. Louis; Eugene E. Weilbacher, Ellisville; Raymond O. Bodicky, Oakville; James G. Schneider, St. Louis, all of Mo.

[73] Assignee: Sherwood Medical Company, St. Louis, Mo.

[21] Appl. No.: 976,705

[22] Filed: Nov. 16, 1992

Related U.S. Application Data

[63] Continuation of Ser. No. 555,969, Jul. 19, 1990, abandoned.

[51] Int. Cl.[5] ........................ A61M 31/00; A61B 5/00

[52] U.S. Cl. ........................ 604/54; 604/167; 604/170; 604/270; 604/283; 128/772

[58] Field of Search ........................ 604/280–284, 604/270, 264–266, 164–170, 29, 54, 82, 83, 93, 95, 181, 905, 912, 43, 44; 128/656–658, 772, 207.1 4, 207.15, 8

[56] References Cited

U.S. PATENT DOCUMENTS

| | | | |
|---|---|---|---|
| 1,596,754 | 8/1926 | Moschelle . | |
| 3,964,488 | 6/1976 | Ring et al. | 128/207.14 |
| 3,973,556 | 8/1976 | Fleischhacker et al. | 128/2 M |
| 3,996,939 | 12/1976 | Sheridan et al. | 128/207.14 |
| 4,033,331 | 7/1977 | Guss et al. | 128/2 M |
| 4,168,703 | 9/1979 | Kenigsberg | 604/280 |
| 4,270,542 | 6/1981 | Plumley | 128/350 R |
| 4,344,428 | 8/1982 | Sherman | 128/207.14 |
| 4,345,602 | 8/1982 | Yoshimura et al. | 604/23 |
| 4,349,024 | 9/1982 | Ralston, Jr. | 128/247 |
| 4,534,363 | 8/1985 | Gold | 128/772 |
| 4,536,179 | 8/1985 | Anderson et al. | 604/266 |
| 4,547,192 | 10/1985 | Brodsky et al. | 604/270 |
| 4,601,713 | 7/1986 | Fuqua | 604/280 |
| 4,610,673 | 9/1986 | Russo | 604/270 |
| 4,613,323 | 9/1986 | Norton et al. | 604/270 |
| 4,636,200 | 1/1987 | Vaillancourt | 604/170 |
| 4,659,328 | 4/1987 | Potter et al. | 604/170 |
| 4,661,110 | 4/1987 | Fortier et al. | 604/256 |
| 4,668,225 | 5/1987 | Russo et al. | 604/270 |
| 4,705,709 | 11/1987 | Vailancourt | 428/36 |
| 4,747,827 | 5/1988 | Micek | 604/54 |
| 4,828,550 | 5/1989 | Kurimoto | 604/270 |
| 4,834,709 | 5/1989 | Banning et al. | 604/281 |
| 4,840,172 | 6/1989 | Augustine et al. | 128/207.14 |
| 4,850,983 | 7/1989 | Brenneman et al. | 604/270 |
| 4,854,330 | 8/1989 | Evans, III et al. | 128/772 |
| 4,874,365 | 10/1989 | Frederick et al. | 604/54 |
| 4,930,521 | 6/1990 | Metzger et al. | 128/786 |
| 4,955,862 | 9/1990 | Sepetka | 128/658 |
| 4,983,170 | 1/1991 | Etheredge, III et al. | 604/270 |
| 4,991,602 | 2/1991 | Amplatz et al. | 128/657 |
| 4,998,919 | 3/1991 | Schnepp-Pesch et al. | 604/280 |
| 5,013,296 | 5/1991 | Buckberg et al. | 604/44 |

FOREIGN PATENT DOCUMENTS

| | | | |
|---|---|---|---|
| 1185862 | 4/1985 | Canada . | |
| 0255234 | of 0000 | European Pat. Off. . | |
| 0591963 | 7/1925 | France | 604/270 |
| 2380034 | 9/1978 | France . | |
| 2064963 | of 0000 | United Kingdom . | |

*Primary Examiner*—C. Fred Rosenbaum
*Assistant Examiner*—Mark Bockelman
*Attorney, Agent, or Firm*—Andrew J. Beck; Montgomery W. Smith; Curtis D. Kinghorn

[57] ABSTRACT

A relatively flexible, dual-lumen enteral feeding tube for delivery of fluid through a patient's esophagus to the patient's digestive system, the enteral feeding tube having proximal and distal ends. The tube comprises an enteral feeding lumen having a feeding lumen inlet opening adjacent the proximal end of the tube and a feeding lumen outlet opening adjacent the distal end of the tube. Additionally, a relatively small stylet lumen is provided separate from said enteral feeding lumen, the stylet lumen having a stylet lumen inlet opening adjacent the proximal end of the tube and being longitudinally co-extensive with a substantial length of the enteral feeding lumen. A relatively stiff stylet having a tapered annealed distal portion is removably positioned in the stylet lumen and extends from the stylet inlet lumen opening to adjacent to the feeding lumen outlet opening. A Y-site adaptor is fixed on the proximal end of the tube and the stylet is shorter in length than the distance from either of the Y-site openings to the tube outlet opening. To facilitate insertion or removal of the stylet, which is constructed of metal, into or from the stylet lumen, a portion of the stylet is provided with a first coating of polytetrafluorethylene having a second coating of silicone over the first coating.

26 Claims, 2 Drawing Sheets

ENTERAL FEEDING TUBE ENTERAL FEEDING TUBE WITH SEPARATE STYLET LUMEN

This is a continuation of copending application(s) Ser. No. 07/555,969 filed on Jul. 19, 1990 Jul. 19, 1990, now abandoned.

FIELD OF THE INVENTION

The present invention relates to an improved enteral feeding tube for delivering nutritional, irrigational, and/or medicinal fluids or the like to the digestive system of a human patient.

BACKGROUND OF THE INVENTION

Enteral feeding tubes are conventionally used for introducing nutritional, irrigational, and/or medicinal fluids through a patient's mouth or nose and esophagus into the patient's digestive system and sometimes for aspiration of fluids therefrom. Such enteral feeding tubes are typically constructed of soft, flexible material to minimize patient discomfort and trauma during insertion and extended placement. Because these tubes are conventionally constructed of soft, flexible material, such as polyurethane or the like, a relatively stiff but narrow metal stylet is conventionally inserted into a relatively large feeding lumen of the tube to stiffen the same to facilitate forcing the tube through the restricted, tortuous path required for movement through the patient's mouth or nose and esophagus for insertion into the patient's stomach or intestines. Such a stylet placement is disclosed in the U.S. Pat. Nos. 4,659,328 to Potter et al and 4,874,365 to Frederick et al. Proper placement of the feeding tube in the digestive system of the patient is sometimes difficult to achieve and is usually ascertained by x-ray, aspiration of gastric contents, auscultation by stethoscope placed over the stomach during air injection or other checking method. If placement appears to be appropriate, the wire stylet is then removed for patient comfort. However, for a number of reasons including improper placement or accidental dislodgement, it is sometimes necessary to reinsert the stylet into the feeding tube to alter the location thereof. Utilizing conventional enteral feeding tubes and stylets, removal, insertion and/or reinsertion of such stylet often proves to be difficult and even dangerous. This is because of insufficient or excessive stylet stiffness, because of friction between the tube lumen and the stylet, and because of the danger of the stylet piercing the tube lumen or protruding through the distal opening of the feeding tube, thereby exposing the stylet and possibly causing injury to the patient. Additionally, re-handling of the stylet after contamination thereof in the feeding lumen of a conventional enteral feeding tube by the patient's bodily fluids is sometimes considered undesirable or disconcerting to health care workers.

SUMMARY OF THE INVENTION

In this light, it is a general object of the present invention to circumvent or solve the problems noted above. In achieving this general object, the present invention provides a relatively flexible, dual-lumen enteral feeding tube for delivering fluids through a patient's esophagus to the patient's digestive system, the enteral feeding tube having proximal and distal ends and comprising a primary or enteral feeding lumen having a feeding lumen inlet opening adjacent the proximal end of the tube and a feeding lumen outlet opening adjacent the distal end of the tube. A secondary or stylet lumen separate from the enteral feeding lumen is additionally provided, the stylet lumen having a stylet lumen opening adjacent the proximal end of the tube and being longitudinally co-extensive with a substantial length of said enteral feeding lumen and closed on its distal end. According to the present invention, a relatively stiff wire stylet is removably positioned in the stylet lumen and extends from the stylet lumen opening to adjacent the feeding lumen outlet opening. Because the wire stylet is positioned in a separate stylet lumen instead of in the enteral feeding lumen, it cannot interfere with fluid flow and the stylet is not contaminated by bodily fluids, as would be the case if the wire stylet were positioned in the enteral feeding lumen as in some prior art devices. Additionally, because the stylet lumen is substantially smaller than the enteral feeding lumen and the stylet is more closely confined therein, in some circumstances this arrangement assists in stiffening the enteral feeding tube to a more appropriate degree than would be the case if the stylet were loosely positioned in the substantially larger enteral feeding lumen.

It is a further object and aspect of the present invention to provide an enteral feeding tube wire stylet with a coating of TEFLON ® polymer (polytetrafluorethylene), over which a lubricous coating of silicone is applied. It is believed that such a lubricous coating arrangement facilitates insertion and/or withdrawal of the stylet to or from the relatively small diameter stylet lumen by reducing the drag of the stylet against the interior of the stylet lumen compared to the drag presented in an arrangement where the silicone is applied directly to the wire stylet for lubrication purposes. Additionally, because the silicone coated stylet is positioned in another lumen separate from the feeding lumen, the silicone is not contaminated by bodily fluids possibly present in the main or enteral feeding lumen.

These and other objects and advantages of the present invention will become apparent from the following detailed description of the present invention when read in conjunction with the accompanying drawings, described as follows.

DETAILED DESCRIPTION OF THE PRESENT INVENTION

Figure 1:
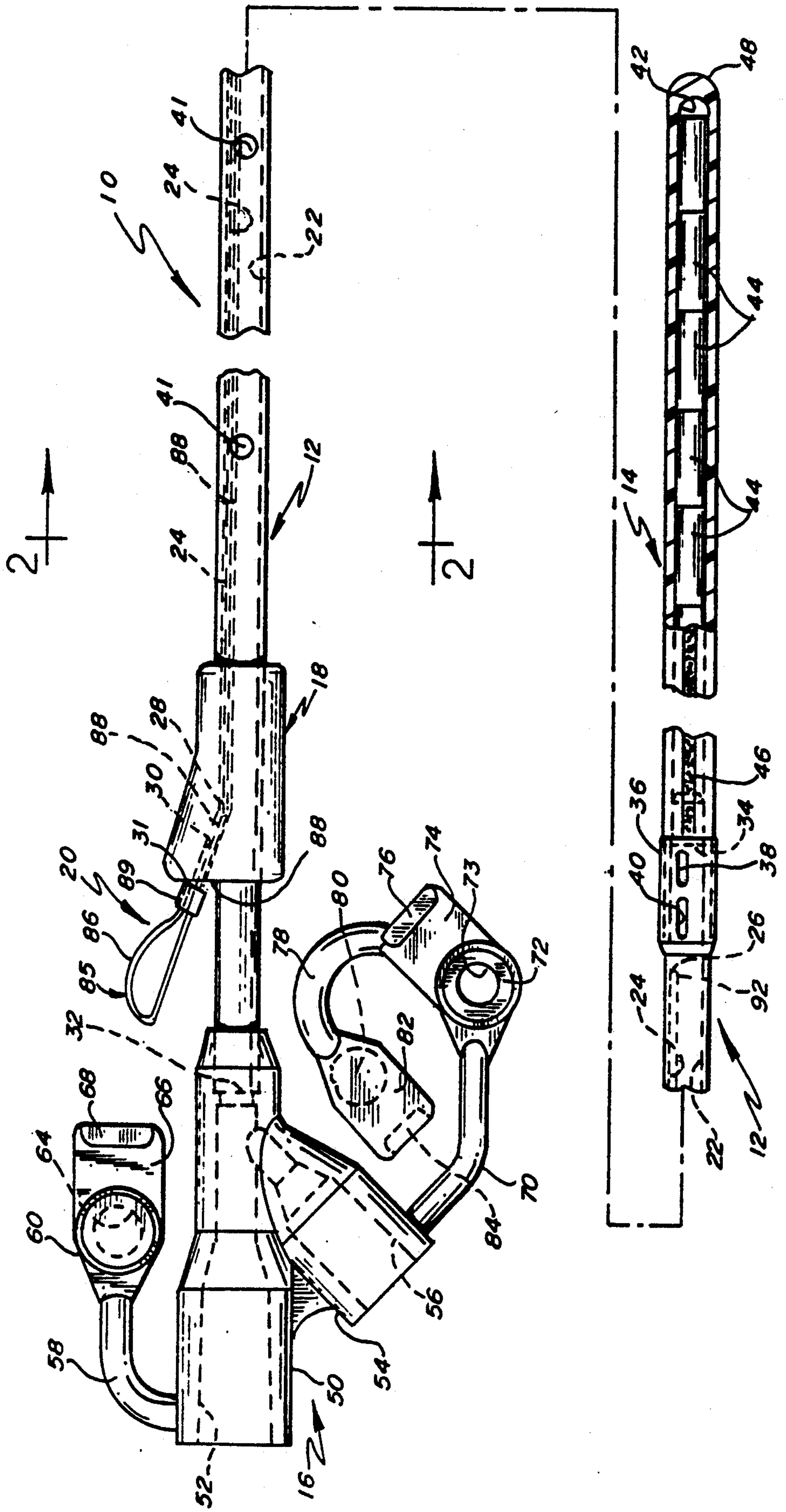
FIG. 1 is a plan view of an improved enteral feeding tube according to the present invention, with portions thereof broken away for illustrative purposes.

Referring in more detail to FIG. 1 of the drawings, there is illustrated therein an improved enteral feeding tube 10 for nasogastric or nasointestinal feeding which basically comprises a relatively flexible, dual-lumen tube assembly 12, to the distal end of which is fixed a conventional bolus weight assembly 14. Fixed to the proximal end of the tube assembly 12 is a Y-site connector, adaptor and closure assembly 16, to the right of which, as shown in FIG. 1, is fixedly positioned a laterally projecting stylet opening saddle 18 having a wire stylet assembly 20 removably positioned therein.

Figure 2:
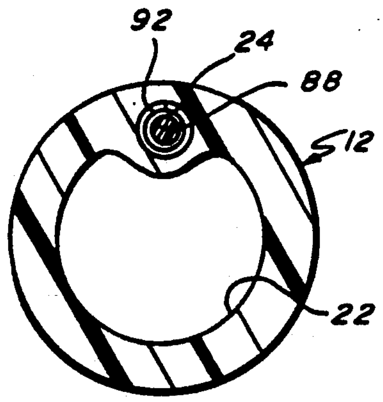
FIG. 2 is a cross-sectional view of the enteral feeding tube shown in FIG. 1 and taken along lines 2—2 therein.

The dual-lumen tube assembly 12 is constructed of a soft, flexible material, such as polyurethane or the like, in relatively small diameters, such as from 8 to 12 French (0.1048 to 0.1572 inch). As best seen in FIG. 2, the tube assembly 12 is hollow and comprises a relatively large diameter primary or enteral feeding lumen 22 adjacent a relatively small diameter, separate secondary or stylet lumen 24, approximately 0.04 inch in diameter the distal end 26 of which is closed as by dead-ending within the tube assembly 12 by a plug or the like. The proximal end 28 of the stylet lumen is in communication with an angularly oriented saddle lumen 30 of a like small diameter extending from the proximal end 28 of the stylet lumen to a stylet lumen inlet opening or port 31 provided in a laterally offset face 33 in the stylet opening saddle 18.

The enteral feeding lumen 22 extends from its proximal end 32 to its distal end 34 adjacent a bolus weight assembly junction 36 fixed between the tube assembly 12 and the bolus weight assembly 14 and through which are provided two longitudinally-spaced enteral feeding lumen outlets 38 and 40 spaced at 180° about the tube periphery in fluid communication with the distal end 34 of the enteral feeding lumen 22. The exterior surface of the tube assembly 12 is provided with a plurality of depth gauge or reference marks 41 to assist in properly positioning the enteral feeding tube 10.

The bolus weight assembly 14 includes a cavity 42 in which are positioned a plurality of conventional cylindrical bolus weights 44 constructed of tungsten and of approximately 0.75 gram each, the function of which is to assist in positioning the enteral feeding tube in the patient's digestive system and maintaining such positioning over an extended period. A radiopaque line 46 may be provided on the surface of the bolus weight assembly 14 to assist in locating the position of the distal end 48 of the enteral feeding tube 10 in a patient by conventional x-ray means or this line 46 may be eliminated because the weights 44 are by their nature radiopaque and therefore make the line 46 unnecessary. Alternately, the tube assembly 12 and bolus weight assembly 14 may be constructed of a plastic material such as DOW PELLETHANE® thermoplastic with Barium Sulfate ($BaSO_4$) mixed throughout such material to provide a radiopaque construction of the entire tube and bolus assemblies. The distal end 48 of the bolus weight assembly 14 is provided with a cushion of soft, flexible material such as polyurethane, and is rounded to avoid trauma to the patient induced by tube insertion or extended placement.

Figure 3:
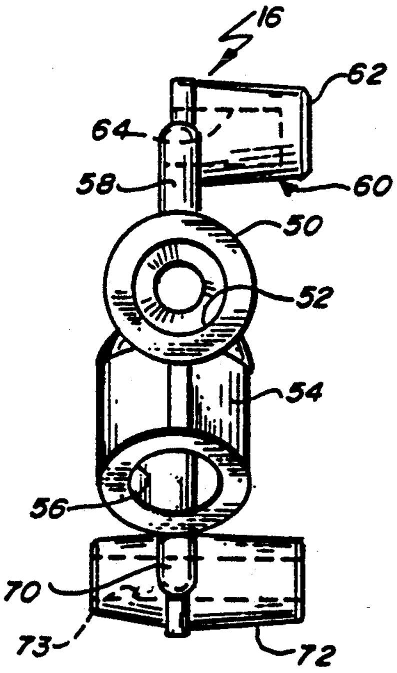
FIG. 3 is a left side view of the enteral feeding tube shown in FIG. 1.

Referring to FIGS. 1 and 3 of the drawings, the Y-site connector, adaptor and closure assembly 16 is constructed of a plastic material such as polyvinyl chloride, or the like and is fixed to the proximal end of the tube assembly 12. The Y-site connector comprises a hollow feeding tube portion 50 including a feeding port lumen 52 in fluid communication with the proximal end 32 of the enteral feeding lumen 22 and an angularly disposed, hollow irrigation tube portion 54 including an irrigation port or lumen 56, the distal end of which is in fluid communication with the distal end of the feeding port lumen 52 and thereby in fluid communication with the proximal end 32 of the enteral feeding lumen 22. The feeding port lumen 52 and irrigation port lumen 56 include larger and adjacent smaller diameter portions which are shaped, sized and adapted to receive a conventional catheter tip syringe and the feeding port lumen is also shaped and sized to receive a standard stepped feeding tube connector of a conventional enteral administration tubing set. The irrigation port lumen 56 is also adapted to receive an adaptor, as will be hereinafter discussed, to facilitate reception of a conventional luer tip syringe, and is adapted to be used for delivery of any irrigational, medicinal, or other prescribed fluids to the patient's digestive system or aspiration of fluids therefrom. Connected to the proximal end of the feeding tube portion 50 by a flexible arm 58 is a cup-shaped closure 60, as best seen in FIG. 3, the closed end 62 of which is adapted to be inserted in the feeding port or lumen 52 with the cup-shaped recess 64 on the exterior side of the closure 60 when seated in the feeding port or lumen 52. It should be noted that by providing the cup-shaped recess 64 on the exterior side of the closure 60, the closure 60 may be conveniently compressed for insertion into the feeding port lumen 52 and withdrawal therefrom. But further, this closure arrangement is considered to be advantageous over prior art closures for feeding lumen wherein the closure is reversed and the cup-shaped recess side of the closure is inserted into a feeding port lumen because when such a reversed closure is removed, the recess sometimes carry a significant amount of patient bodily fluid contaminants accumulated in the recess by virtue of fluid communication of the recess with the interior of a feeding port lumen, and thereby exposing a health care worker to contact with such contaminants. The distal end of flexible arm 58 further includes a web 66 extending beyond the closure 60, the web being provided with a finger-grip projection 68 to facilitate insertion and withdrawal of the closure 60 in or from the feeding port lumen 52.

Connected to the proximal end of the irrigation tube portion 54 is a flexible arm 70 and a hollow tubular adaptor 72, having a bore 73 therein, the adaptor being shaped and sized to be positioned in the irrigation port lumen 56 to reduce the size thereof to facilitate sealing engagement with a luer slip or luer lock tip of a syringe. Connected to the arm 70 and the adaptor 72 is a web 74 having a finger-grip projection 76 to facilitate insertion and withdrawal of the adaptor 72 in or from the irrigation port lumen 56. Connected to the outer end of the web 74 is a second flexible arm 78, as shown in FIG. 1, which is connected to a solid cylindrical closure or plug 80, shaped and sized for insertion into and sealing engagement with the bore 73 of the hollow tubular adaptor 72. The plug 80 is supported on a web 82, the outer end of which is provided with a finger-grip projection 84 to facilitate insertion or withdrawal of the plug 80 from the bore 73 of the hollow tubular adaptor 72.

Figure 5:
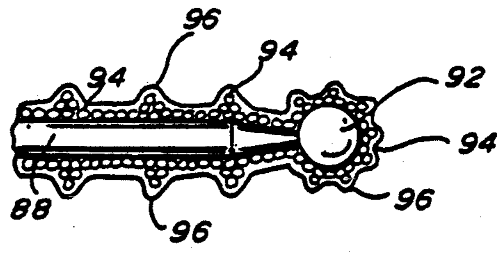
FIG. 5 is a schematic illustration on an enlarged scale of the distal tip portion of the wire stylet shown in FIG. 4 but shown with TEFLON ® and silicone coatings schematically represented on the stylet according to the present invention.
Figure 4:
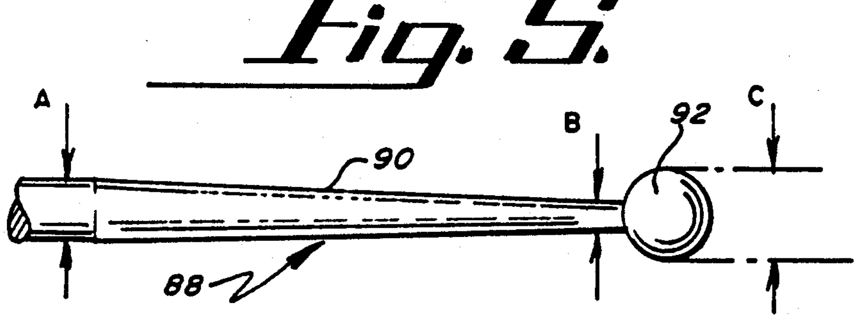
FIG. 4 is plan view, on an enlarged scale, of a distal tip portion of a wire stylet of the enteral feeding tube shown in FIG. 1.

Referring to FIGS. 1 and 4 of the drawings, the wire stylet assembly 20 comprises a stainless steel wire 85 of appropriate strength (290,000 to 300,000 P.S.I. tensile strength) and rigidity to appropriately stiffen the enteral feeding tube 10 for insertion through the nose or mouth, the esophagus and into the stomach or small intestines. The wire 85 is fully hardened along the full length thereof except adjacent the distal end thereof which will be subsequently discussed. The proximal free end of the wire 85 is looped back on itself to form a finger pull or wire loop 86 by fixing the free end to the shaft 88 of the wire 85 by positioning the free end and the adjacent portion of the shaft 88 in an appropriately sized section of heat shrink tubing 89 having an adhesive-coating on the inner surface thereof and heating the same to shrink the tubing 89 and thereby fix the free end to the shaft 88. Such heat shrink tubing may be like FIT® 321 shrinkable polyolefin tubing sold by Alpha Wire Corporation, or equivalent. The wire loop 86 is positioned on the proximal exterior side of the stylet opening saddle 18 when the stylet is inserted in the stylet lumen inlet opening 30 and bottomed in the stylet lumen 24. It should be noted that the stylet opening saddle is longitudinally spaced and laterally offset from the Y-site connector for convenience on stylet insertion. Additionally, this positioning, as opposed to a location in the Y-site connector, avoids obstructing or interference with use of the Y-site or primary lumen for other, more usual, purposes. The distal end 90 of the wire 85, as shown in FIG. 4, is tapered in a converging manner commencing at a point about three inches from the distal end to enhance the flexibility thereof to meet the requirement of the tortuous path of tube insertion and is fixedly connected at its distal end, as by plasma welding, to a spherical stylet globe 92. The diameter of the wire shaft 88 at point "A" as indicated in FIG. 4, is about 0.02 inch, at point "B" is about 0.01 inch and the diameter of the globe 92 is about 0.022 inch the globe 92 is shaped and sized to make piercing of the tube assembly 12 unlikely. To further minimize the possibly of piercing of the tube assembly 12, approximately the last two (2) inches of the distal end 90 of the wire 85 is fully annealed to completely soften the stainless steel to induce stylet deformation rather than tube piercing. In the annealed condition, the tensile strength of the annealed portion is reduced to 60,000 to 100,000 P.S.I. The globe 92 provides a relatively snug fit for the distal end of the stylet in the distal end 26 of the stylet lumen 24 (as compared to positioning of the stylet in the relatively larger enteral feeding lumen) to enhance the stiffening effect of the stylet. Referring to FIG. 5, at least those portions of the wire stylet assembly 20 adapted to be positioned within the stylet lumen 24 are first coated with a layer of TEFLON® polymer (polytetrafluorethylene), over which is provided a second coating of silicone medical fluid or the like to provide a lubricant to facilitate insertion and withdrawal of the wire stylet assembly 20 into or from the relatively small stylet lumen 24. It is believed that such lubrication is enhanced because, as schematically illustrated in FIG. 4, the TEFLON® particles 94 schematically illustrated as small circles in FIG. 4, are unevenly deposited along the metal wire stylet assembly 20 so that some particles of TEFLON® are elevated relative to the remainder thereof. Over this uneven surface, a continuous layer of a silicone medical fluid 96 (such as Dow Corning 360 silicone medical fluid, or equivalent) is deposited to provide a lubricous coating on the stylet. Although not fully understood, it is believed that because some of the particles 94 of TEFLON® polymer are laterally elevated relative to others, these elevated particles having a silicone coating thereon are the primary ones making contact with the walls of the stylet lumen 24, with the less elevated particles not making contact, thereby reducing drag exerted by the wall against the stylet during insertion and/or withdrawal. It should also be noted that the wire stylet assembly 20 is substantially shorter than the distance between the Y-site feeding and irrigation ports 52 and 56 and the outlet openings 38 and 40, so that even if the stylet assembly 20 was erroneously or accidentally inserted in the feeding lumen 22, the distal end globe 92 would not reach the feeding lumen outlet openings 38 and 40, so that no danger exists that the stylet tip could project through the openings 38 and 48 and thereby possibly injure a patient.

It should also be noted that although the metal wire stylet of the present invention is coated with a silicone medical fluid for lubrication purposes, because the wire stylet is advantageously segregated in a separate stylet lumen and not positioned in the enteral feeding lumen, any danger of enteral feeding or irrigation fluids washing such silicone into the patient's digestive system is eliminated, as might be the case if the silicone-coated stylet were positioned in the feeding lumen.

While the invention has been described in connection with one embodiment, one skilled in the art should appreciate that the invention is not necessarily so limited and that other embodiments or modifications thereof may be provided without departing from the inventive concept of the present invention, which is to be determined by reference to the following claims.

What is claimed is:

1. A relatively flexible enteral feeding tube for delivery of fluid through a patient's esophagus to the patient's intestinal tract, said enteral feeding tube having proximal and distal ends, said enteral feeding tube comprising:

an enteral feeding lumen having a feeding lumen inlet opening adjacent said proximal end of said tube and at least one feeding lumen outlet opening adjacent said distal end of said tube;

a stylet lumen separate from said enteral feeding lumen, said stylet lumen having a stylet lumen inlet opening adjacent said proximal end of said tube, said stylet lumen being closed except for said stylet lumen inlet opening, said stylet lumen being longitudinally co-extensive with a substantial length of said enteral feeding lumen, said stylet lumen having a diameter substantially less than the diameter of said enteral feeding lumen;

a relatively stiff stylet having a proximal end and a distal end, said stylet removably positioned in said stylet lumen and extending from said stylet lumen inlet opening to adjacent said feeding lumen outlet opening, said stylet having a first coating of polytetrafluorethylene applied to and about said stylet and a second coating of silicone applied over and about said polytetrafluorethylene coating, said stylet having a tapered portion of reducing diameter adjacent to and narrowing towards said distal end of said stylet to enhance the flexibility thereof, said stylet also having a relatively enlarged globe on said distal end of said stylet, said globe having a diameter slightly less than the diameter of said stylet lumen.

2. An enteral feeding tube according to claim 1 wherein said enteral feeding tube further includes a Y-site adaptor fixed to said proximal end of said enteral feeding tube, said Y-site adaptor including two angularly coverging lumen in fluid communication with said enteral feeding lumen, each of said angularly converging lumen having a Y-site adaptor inlet opening thereon for providing access to said enteral feeding lumen through said Y-site adaptor.

3. A relatively flexible enternal feeding tube for delivery of fluid through a patient's esophagus to the patient's intestinal tract, said enteral feeding tube having proximal and distal ends, said enteral feeding tube comprising:

an enteral feeding lumen having a feeding lumen inlet opening adjacent said proximal end of said tube and at least one feeding lumen outlet opening adjacent said distal end of said tube;

a stylet lumen separate from said enteral feeding lumen, said stylet lumen having a stylet lumen inlet opening adjacent said proximal end of said tube and being longitudinally co-extensive with a substantial length of said enteral feeding lumen;

a relatively stiff stylet having a proximal end and a distal end, said stylet removably positioned in said stylet lumen and extending from said stylet lumen inlet opening to adjacent said feeding lumen outlet opening;

a Y-site adaptor fixed to said proximal end of said enteral feeding tube, said Y-site adaptor including two angularly converging lumen in fluid communication with said enteral feeding lumen, each of said angularly converging lumen having a Y-site adaptor inlet opening thereon for providing access to said enteral feeding lumen through said Y-site adaptor; and, a first closure means adapted to be inserted in at least one of said Y-site adaptor inlet openings, said first closure means including a generally cup-shaped closure having a generally cup-shaped recessed portion extending into said cup-shaped closure from the exterior surface of said first closure means, said cup-shaped closure insertable into said Y-site adaptor inlet opening to close said Y-site adaptor opening, and a flexible arm connecting said first closure means to said Y-site adaptor.

4. An enteral feeding tube according to claim 3 wherein said relatively stiff stylet is constructed of metal and is shorter in length than the distance from either of said inlet openings of said Y-site adaptor to said outlet opening of said enteral feeding lumen.

5. An enteral feeding tube according to claim 3 wherein said stylet lumen inlet opening is longitudinally spaced from, and laterally offset from, said Y-site adaptor.

6. An enteral feeding tube according to claim 3 further including: a hollow, tubular adaptor having a longitudinally extending, generally cylindrical bore therethrough, said tubular adaptor adapted to be inserted into one of said Y-site adaptor inlet openings, said bore adapted to receive a distal end of a syringe; means for connecting said tubular adaptor to said Y-site adaptor; and, a second closure means adapted to be inserted in said generally cylindrical bore.

7. An enteral feeding tube as in claim 3 further characterized in that at least one of said Y-site adaptor inlet openings is adapted to receive nutritional fluid from an enteral administration tubing set.

8. A relatively flexible enteral feeding tube for delivery of fluid through a patient's esophagus to the patient's intestinal tract, said enteral feeding tube having proximal and distal ends, said enteral feeding tube comprising:

an enteral feeding lumen having a feeding lumen inlet opening adjacent said proximal end of said tube and at least one feeding lumen outlet opening adjacent said distal end of said tube;

a stylet lumen separate from said enteral feeding lumen, said stylet lumen having a stylet lumen inlet opening adjacent said proximal end of said tube and being longitudinally co-extensive with a substantial length of said enteral feeding lumen, said stylet lumen being closed except for said stylet lumen inlet opening; and, a relatively stiff metal stylet having a proximal end and a distal end, said stylet removably positioned in said stylet lumen and extending from said stylet lumen inlet opening to adjacent said feeding lumen outlet opening, said distal end of said stylet being annealed to soften the distal portion of said stylet, said stylet including a tapered portion of reducing diameter adjacent to and narrowing toward the distal end of said stylet to enhance the flexibility thereof, said stylet having a relatively enlarged globe on the distal end of said stylet, said globe having a diameter slightly less than the diameter of said stylet lumen.

9. An enteral feeding tube according to claim 8 wherein said stylet is constructed of metallic wire and further includes a wire loop on the proximal end thereof, the free end of said wire forming said loop being fixed to a straight portion of said wire by a heat shrinkable tubing having an adhesive coating on the wiring contacting inner face of said tubing.

10. A relatively flexible enteral feeding tube for delivery of fluid through a patient's esophagus to the patient's intestinal tract, said enteral feeding tube having proximal and distal ends, said enteral feeding tube sized for insertion of said distal end through the nasal canal and esophagus into the patient's intestinal tract, said enteral feeding tube being constructed of a relatively soft, relatively flexible material to allow said enteral feeding tube to be forced through the restricted, tortuous path between a patient's mouth or nose and the patient's intestinal tract, said enteral feeding tube comprising:

an enteral feeding lumen having a feeding lumen inlet opening adjacent said proximal end of said tube and at least one feeding lumen outlet opening adjacent said distal end of said tube, said enteral feeding lumen being sized to allow enteral feeding fluid to pass therethrough;

a stylet lumen separate from said enteral feeding lumen, said stylet lumen having a stylet lumen inlet opening adjacent said proximal end of said tube and being longitudinally co-extensive with a substantial length of said enteral feeding lumen, said stylet lumen being closed except for said stylet lumen inlet opening; and, a relatively stiff stylet having a proximal end and a distal end, said stylet removably positioned in said stylet lumen and extending from said stylet lumen inlet opening to adjacent said feeding lumen outlet opening, said stylet including a first coating of polytetrafluorethylene applied to and about said stylet and a second coating of silicone applied over and about said polytetrafluorethylene coating.

11. An enteral feeding tube according to claim 10, further including bolus weight means attached to the distal end of the enteral feeding tube.

12. An enteral feeding tube according to claim 10 wherein said enteral feeding lumen has a diameter substantially greater than the diameter of said stylet lumen.

13. An enteral feeding tube according to claim 10 wherein said enteral feeding tube further includes a Y-site adaptor fixed to said proximal end of said enteral feeding tube, said Y-site adaptor including two angularly converging lumen in fluid communication with said enteral feeding lumen, each of said angularly converging lumen having an inlet opening on the proximal end thereof, at least one of said opening being adapted to receive nutritional fluid from an enteral administration tubing set.

14. An enteral feeding tube according to claim 10 wherein said stylet is constructed of metallic wire.

15. An enteral feeding tube according to claim 14 wherein said stylet is constructed of stainless steel and includes a tapered portion of reducing diameter adjacent to and narrowing toward the distal end to enhance the flexibility thereof, a distal portion of said tapered portion being annealed to soften the same and a relatively enlarged ball on the distal end of said tapered portion, said ball having a diameter only slightly less than the diameter of said stylet lumen.

16. An enteral feeding tube ad in claim 14 further characterized in that a distal portion of said stylet is annealed to soften the distal portion of said stylet.

17. A tube ad in claim 14 characterized in that said stylet includes a wire loop on said proximal end of said stylet, said loop being fixed to a straight portion of said metallic wire by a heat shrinkable tubing having an adhesive coating on the face of said tubing contacting said metallic wire.

18. An enternal feeding tube as in claim 10 wherein said stylet includes a tapered portion of reducing diameter adjacent to and narrowing toward the distal end of said stylet to enhance the flexibility thereof.

19. An enteral feeding 10 tube as in claim 10 wherein said stylet has a relatively enlarged globe on the distal end of said stylet, said globe having a diameter slightly less than the diameter of said stylet lumen.

20. An enteral feeding tube according to claim 10 wherein said enteral feeding lumen has a diameter substantially greater than the diameter of said stylet lumen.

21. An improvement in a relatively flexible enteral feeding tube for delivering fluid through a patient's esophagus to the patient's intestinal tract, said enteral feeding tube having proximal end distal ends and at least one enteral feeding tube lumen extending from adjacent said proximal end of said tube to adjacent said distal end of said tube, said enteral feeding tube lumen having an inlet opening adjacent said proximal end of said tube, said improvement comprising:

a relatively stiff wire stylet removably positioned in said enteral feeding tube lumen and extending from said inlet opening to adjacent said distal end of said tube, said stylet having a first coating of polytetrafluorethylene applied to and about said wire stylet and a second coating of silicone applied over and about said polytetrafluorethylene coating; and wherein said enteral feeding tube further includes a Y-site adaptor fixed to said proximal end of said enteral feeding tube, said Y-site adaptor including two angularly converging adaptor lumen in fluid communication with said enteral feeding tube lumen, each of said angularly converging adaptor lumen having a Y-site adaptor inlet opening thereon for providing access to said enteral feeding lumen through said Y-site adaptor.

22. A relatively flexible enteral feeding tube for delivery of fluid through a patient's esophagus to the patient's intestinal tract, said enteral feeding tube having proximal and distal ends, said enteral feeding tube comprising:

an enteral feeding lumen having a feeding lumen inlet opening adjacent said proximal end of said tube and at least one feeding lumen outlet opening adjacent said distal end of said tube;

a stylet lumen separate from said enteral feeding lumen, said stylet lumen having a stylet lumen inlet opening adjacent said proximal end of said tube and being longitudinally co-extensive with a substantial length of said enteral feeding lumen;

a relatively stiff stylet having a proximal end and a distal end, said stylet removably positioned in said stylet lumen and extending from said stylet lumen inlet opening to adjacent said feeding lumen outlet opening;

a Y-site adaptor fixed to said proximal end of said enteral feeding tube, said Y-site adaptor including two angularly converging lumen in fluid communication with said enteral feeding lumen, each of said angularly converging lumen having a Y-site adaptor inlet opening thereon for providing access to said enteral feeding lumen through said Y-site adaptor;

a hollow, tubular adaptor having a longitudinally extending, generally cylindrical bore therethrough, said tubular adaptor adapted to be inserted into one of said Y-site adaptor inlet openings, said bore adapted to receive a distal end of a syringe;

means for connecting said tubular adaptor to said Y-site adaptor; and, a second closure means adapted to be inserted in said generally cylindrical bore.

23. A relatively flexible enteral feeding tube for delivery of fluid through a patient's esophagus to the patient's intestinal tract, said enteral feeding tube having proximal and distal ends, said enteral feeding tube comprising:

an enteral feeding lumen having a feeding lumen inlet opening adjacent said proximal end of said tube and at least one feeding lumen outlet opening adjacent said distal end of said tube;

a stylet lumen separate from said enteral feeding lumen, said stylet lumen having a stylet lumen inlet opening adjacent said proximal end of said tube and being longitudinally co-extensive with a substantial length of said enteral feeding lumen;

a relatively stiff stylet having a proximal end and a distal end, said stylet removably positioned in said stylet lumen and extending from said stylet lumen inlet opening to adjacent said feeding lumen outlet opening, said stylet having a first coating of polytetrafluorethylene applied to and about said stylet and a second coating of silicone applied over and about said polytetrafluorethylene coating; and, a Y-site adaptor fixed to said proximal end of said enteral feeding tube, said Y-site adaptor including two angularly converging lumen in fluid communication with said enteral feeding lumen, each of said angularly converging lumen having a Y-site adaptor inlet opening thereon for providing access to said enteral feeding lumen through said Y-site adaptor.

24. A method for placing fluids in a patient's intestinal tract comprising the steps of:

placing a stylet in a stylet lumen inlet opening of a stylet lumen of a relatively flexible tube having a proximal end and a distal end, the tube having at least a fluid lumen and a stylet lumen separate from the fluid lumen, the fluid lumen having a fluid lumen inlet opening adjacent the proximal end of the tube and at least one fluid lumen outlet opening adjacent the distal end of the tube, said flexible tube further including a Y-site adaptor fixed to said proximal end of said flexible tube, said Y-site adaptor including two angularly converging lumen in fluid communication with said fluid lumen, each of said angularly converging lumen having a Y-site adaptor inlet opening thereon for providing access to said fluid lumen through said Y-site adaptor, the stylet lumen inlet opening located adjacent the proximal end of the tube, the stylet lumen longitudinally co-extensive with a substantial length of the fluid lumen so that the stylet extends from the stylet lumen inlet opening to a point adjacent the fluid lumen outlet opening, said stylet lumen being closed except for said stylet inlet opening;

pushing the distal end of the tube containing the stylet located in the stylet lumen through a patient's nostril and down the patient's alimentary tract to the patient's intestinal tract;

removing the stylet form the stylet lumen while leaving the tube in position through the patient's nostril, alimentary tract, and intestinal tract; and connecting the fluid lumen inlet opening to a source of fluid through the Y-site adaptor whereby fluid passes from the source of fluid through the Y-site adaptor and the fluid lumen to the fluid lumen outlet opening where the fluid leaves the tube and enters the patient's intestinal tract.

25. A method for placing fluids in a patient's intestinal tract comprising the steps of:

placing a stylet in a stylet lumen inlet opening of a stylet lumen of a relatively flexible tube having a proximal end and a distal end, the tube having at least a fluid lumen.and a stylet lumen separate from the fluid lumen, the fluid lumen having a fluid lumen inlet opening adjacent the proximal end of the tube and at least one fluid lumen outlet opening adjacent the distal end of the tube, the stylet being relatively stiff and having a proximal end and a distal end, the stylet extending from the stylet lumen inlet opening to adjacent the feeding lumen outlet opening, the stylet having a first coating of polytetrafluorethylene applied to and about the stylet and a second coating of silicone applied over and about the polytetrafluorethylene coating, the stylet having a tapered portion of reducing diameter adjacent to and narrowing towards the distal end of the stylet to enhance the flexibility thereof, the stylet also having a relatively enlarged globe on the distal end of the stylet, the globe having a diameter slightly less than the diameter of the stylet lumen, the stylet lumen being longitudinally co-extensive with a substantial length of the fluid lumen so that the stylet extends from the stylet lumen inlet opening to a point adjacent the fluid lumen outlet opening, the stylet lumen being closed except for the stylet inlet opening;

pushing the distal end of the tube containing the stylet located in the stylet lumen through a patient's nostril and down the patient's alimentary tract to the patient's intestinal tract;

removing the stylet from the stylet lumen while leaving the tube in position through the patient's nostril, alimentary tract, and intestinal tract; and connecting the fluid lumen inlet opening to a source of fluid through the fluid lumen inlet opening whereby fluid passes from the source of fluid through the fluid lumen inlet opening and the fluid lumen to the fluid lumen outlet opening where the fluid leaves the tube and enters the patient's intestinal tract.

26. A method for placing fluids in a patient's intestinal tract comprising the steps of:

placing a stylet in a stylet lumen inlet opening of a stylet lumen of a relatively flexible tube having a proximal end and a distal end, the tube having at least a fluid lumen and a stylet lumen separate from the fluid lumen, the fluid lumen having a fluid lumen inlet opening adjacent the proximal end of the tube and at least one fluid lumen outlet opening adjacent the distal end of the tube, the stylet being relatively stiff and having a proximal end and a distal end, the stylet extending from the stylet lumen inlet opening to adjacent the feeding lumen outlet opening, the distal end of the stylet being annealed to soften the distal portion of the stylet, the stylet including a tapered portion of reducing diameter adjacent to and narrowing toward the distal end of the stylet to enhance the flexibility thereof, the stylet having a relatively enlarged globe on the distal end of the stylet, the globe having a diameter slightly less than the diameter of the stylet lumen, the stylet lumen being longitudinally co-extensive with a substantial length of the fluid lumen so that the stylet extends from the stylet lumen inlet opening to a point adjacent the fluid lumen outlet opening, the stylet lumen being closed except for the stylet inlet opening;

pushing the distal end of the tube containing the stylet located in the stylet lumen through a patient's nostril and down the patient's alimentary tract to the patient's intestinal tract;

removing the stylet from the stylet lumen while leaving the tube in position through the patient's nostril, alimentary tract, and intestinal tract; and connecting the fluid lumen inlet opening to a source of fluid through the fluid lumen inlet opening whereby fluid passes from the source of fluid through the fluid lumen inlet opening and the fluid lumen to the fluid lumen outlet opening where the fluid leaves the tube and enters the patient's intestinal tract.

* * * * *

UNITED STATES PATENT AND TRADEMARK OFFICE

CERTIFICATE OF CORRECTION

PATENT NO. : 5,242,389

DATED : Sep. 7, 1993

INVENTOR(S) : Eugene F. Schrader; Eugene E. Weilbacher; Raymond O. Bodicky and James G. Schneider It is certified that error appears in the above-indentified patent and that said Letters Patent is hereby corrected as shown below:

On the Title Page, Item [54] and column 1, line 1, replace the title with "Enteral Feeding Tube With Separate Stylet Lumen"

Signed and Sealed this

Thirty-first Day of May, 1994

*Attest:*

BRUCE LEHMAN

*Attesting Officer* *Commissioner of Patents and Trademarks*